(12) United States Patent
Park et al.

(10) Patent No.: US 10,617,590 B2
(45) Date of Patent: Apr. 14, 2020

(54) MOTION ASSISTANCE APPARATUS

(71) Applicant: Samsung Electronics Co., Ltd., Suwon-si, Gyeonggi-do (KR)

(72) Inventors: Youngjin Park, Seoul (KR); Jeonghun Kim, Suwon-si (KR); Seungyong Hyung, Yongin-si (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 131 days.

(21) Appl. No.: 15/592,409

(22) Filed: May 11, 2017

(65) Prior Publication Data

US 2018/0177668 A1 Jun. 28, 2018

(30) Foreign Application Priority Data

Dec. 26, 2016 (KR) .................. 10-2016-0179475

(51) Int. Cl.
*A61H 3/00* (2006.01)
*A61H 1/02* (2006.01)
*A61F 2/70* (2006.01)

(52) U.S. Cl.
CPC .............. *A61H 3/00* (2013.01); *A61F 2/70* (2013.01); *A61H 1/024* (2013.01); *A61H 1/0255* (2013.01); *A61H 1/0262* (2013.01); *A61H 2201/0192* (2013.01); *A61H 2201/123* (2013.01); *A61H 2201/1215* (2013.01); *A61H 2201/163* (2013.01); *A61H 2201/165* (2013.01); *A61H 2201/1642* (2013.01)

(58) Field of Classification Search
CPC combination set(s) only.
See application file for complete search history.

(56) References Cited

U.S. PATENT DOCUMENTS

| 7,537,573 | B2 | 5/2009 | Horst |
| 7,828,755 | B2 | 11/2010 | Ikeuchi |
| 8,986,233 | B2 | 3/2015 | Aoki et al. |
| 9,161,880 | B2 | 10/2015 | Ashihara et al. |
| 2009/0062884 | A1 | 3/2009 | Endo et al. |
| 2011/0066088 | A1 | 3/2011 | Little et al. |
| 2012/0157894 | A1* | 6/2012 | Hiki ............... A61H 1/024 601/35 |

(Continued)

FOREIGN PATENT DOCUMENTS

| EP | 1 637 114 A1 | 3/2006 |
| EP | 1 902 700 A1 | 3/2008 |
| JP | 4874241 B2 | 2/2012 |

(Continued)

OTHER PUBLICATIONS

Extended European Search Report dated Jan. 4, 2018 for EP Application No. 17180092.3.

(Continued)

*Primary Examiner* — Yashita Sharma
(74) *Attorney, Agent, or Firm* — Harness, Dickey and Pierce, P.L.C.

(57) ABSTRACT

Provided is a motion assistance apparatus including a first support configured to support a first part of a user, a connection link rotatably connected to the first support, a second support configured to support a second part of a user, and a distance adjustment assembly configured to adjust a distance from the second support to the connection link.

18 Claims, 20 Drawing Sheets

(56) References Cited

U.S. PATENT DOCUMENTS

2015/0272809 A1  10/2015  Accoto et al.

FOREIGN PATENT DOCUMENTS

| | | |
|---|---|---|
| JP | 2012-165986 A | 9/2012 |
| JP | 2013208342 A | 10/2013 |
| KR | 1020120044683 | 5/2012 |
| KR | 101315199 B1 | 10/2013 |
| KR | 1020150085357 | 7/2015 |
| WO | WO-2012/070244 A1 | 5/2012 |
| WO | WO-2015/019485 A1 | 2/2015 |
| WO | WO-2015/136214 A1 | 9/2015 |

OTHER PUBLICATIONS

Ikeuchi, Yasushi et al., "Walking Assist Device with Bodyweight Support System", The 2009 IEEE/RSJ International Conference on Intelligent Robots and Systems (IROS), St. Louis, MO, Oct. 11-15, 2009, pp. 4073-4079.

Hong, Yun-Pyo et al., "The SoftGait: A Simple and Powerful eight-Support Device for Walking and Squatting", 2015 IEEE/RSJ International Conference on Intelligent Robots and Systems (IROS), Sep. 28-Oct. 2, 2015, pp. 6336-6341, Hamburg, Germany.

Office Action issued from the European Patent Office dated Jun. 18, 2019 for the corresponding EP Application No. 17 180 092.3.

\* cited by examiner

MOTION ASSISTANCE APPARATUS

CROSS-REFERENCE TO RELATED APPLICATION

This application claims priority under 35 U.S.C. § 119 to Korean Patent Application No. 10-2016-0179475, filed on Dec. 26, 2016, in the Korean Intellectual Property Office, the entire contents of which are incorporated herein by reference in their entirety.

BACKGROUND

1. Field

At least one example embodiment relates to a motion assistance apparatus.

2. Description of the Related Art

Motion assistance apparatuses enabling the elderly and/or patients having joint problems to walk with less effort, and motion assistance apparatuses increasing muscular strength of users for military purposes are being developed.

SUMMARY

Some example embodiments relate to a motion assistance apparatus.

In some example embodiment, the motion assistance apparatus may include a first support configured to support a first part of a user; a connection link rotatably connected to the first support; a second support configured to support a second part of a user; and a distance adjustment assembly configured to adjust a distance between the second support and the connection link.

In some example embodiment, a first end and a second end of the distance adjustment assembly are rotatably connected to the connection link and the second support, respectively.

In some example embodiment, the distance adjustment assembly includes a first adjustment link rotatably connected to the connection link; and a second adjustment link having a first end and a second end, the first end of the second adjustment link being movable connected to the first adjustment link, and the second end of the second adjustment link being rotatably connected to the second support.

In some example embodiment, the second adjustment link is rotatably connected to the first adjustment link, and the motion assistance apparatus further includes an actuator configured to generate a power to rotate at least one of the first adjustment link and the second adjustment link.

In some example embodiment, the actuator is between the first adjustment link and the second adjustment link.

In some example embodiment, the second adjustment link is slidably connected to the first adjustment link.

In some example embodiment, the motion assistance apparatus further includes a linear-actuator configured to connect the first adjustment link and the second adjustment link.

In some example embodiment, the motion assistance apparatus further includes a rotation limiter configured to limit a minimum angle between the first adjustment link and the connection link.

In some example embodiment, the motion assistance apparatus further includes an actuator configured to drive the distance adjustment assembly, wherein the first adjustment link and the connection link are configured to perform a single rigid body motion and the connection link is configured to rotate relative to the first support, if an angle between the first adjustment link and the connection link is the minimum angle while the actuator is driven.

In some example embodiment, the rotation limiter includes a shock-absorbing member configured to absorb a shock occurring when the first adjustment link and the connection link perform the single rigid body motion.

In some example embodiment, the motion assistance apparatus further includes the rotation limiter is connected to at least one of the first adjustment link and the connection link and is between the first adjustment link and the connection link.

In some example embodiment, the first support includes a dropping preventer configured to support a portion of the connection link.

In some example embodiment, the motion assistance apparatus further includes an elastic body configured to provide an elastic force to interfere with the connection link splaying from the first support.

In some example embodiment, the motion assistance apparatus further includes a third support configured to support a third part of the user located on an opposite side of the user from the second part; and a connecting member configured to connect the third support and the second support.

In some example embodiment, the first support is configured to support a forefoot of the user and the second support is configured to support a thigh or a portion above the thigh of the user.

In some example embodiment, a portion connecting the distance adjustment assembly and the connection link is located between the forefoot and a heel of the user when the user is wearing the motion assistance apparatus.

In some example embodiment, the motion assistance apparatus further includes a heel guide configured to extend from the distance adjustment assembly in a direction opposite to the connection link, and to contact a ground when the user performs a heel-strike motion.

In some example embodiment, the motion assistance apparatus further includes the heel guide has an arc shape curved upward as a distance from the distance adjustment assembly increases.

In some example embodiment, in a heel strike interval, the heel guide is configured to contact the ground and the first support is configured to separate from the ground, and in a push-off interval, the heel guide is configured to separate from the ground and the first support is configured to contact the ground.

In some example embodiment, the motion assistance apparatus further includes a sensor configured to sense a gait cycle of the user; and a controller configured to control an actuator based on the gait cycle sensed by the sensor such that the controller is configured to turn the actuator on in a stance phase, and to turn the actuator off in a swing phase.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
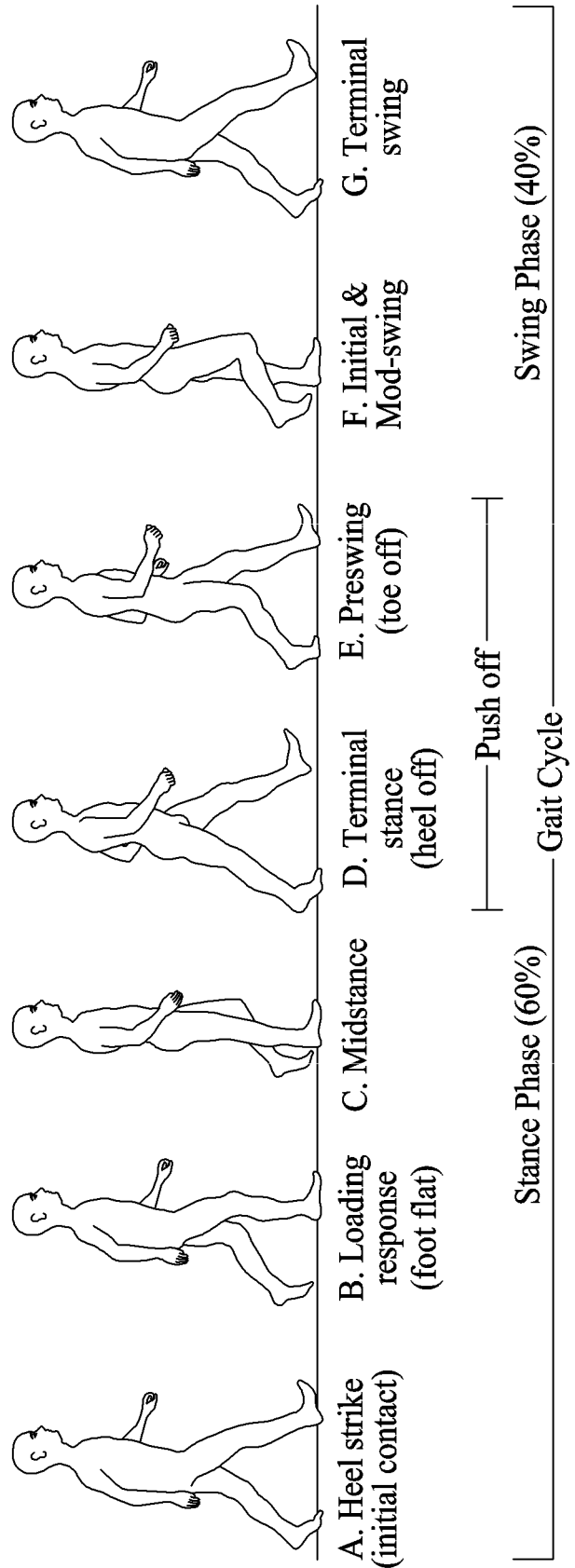
FIG. 1 is a diagram illustrating a gait cycle according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

FIG. 1 is a diagram illustrating a gait cycle according to at least one example embodiment.

Referring to FIG. 1, a gait cycle of a person may be understood that a stance phase in which a leg contacts a ground and a swing phase in which the leg is separated from the ground are repeated by turns. In a human gait, a motion of at least one joint may be performed. For example, when a person is walking, motions of a talocrural joint, a subtalr joint, a knee joint, and/or a hip joint may be performed simultaneously. In this example, each of the joints may have a different degree of freedom and a motion. Thus, to assist the gait based on the motion of each of the joints, an angle of the corresponding joint and a torque applied to the corresponding joint may need to be considered.

Figure 2:
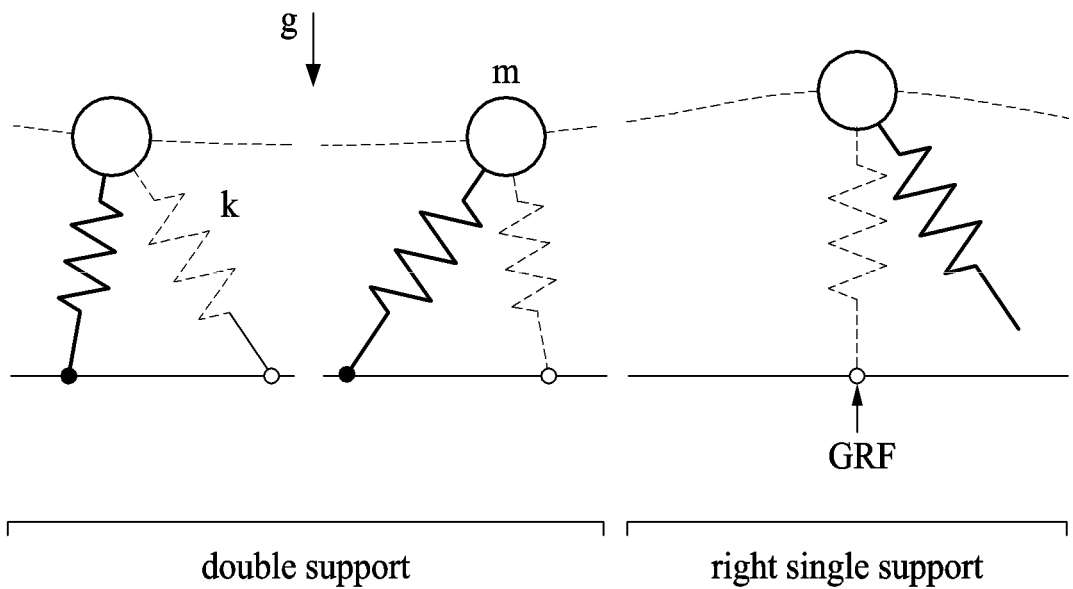
FIG. 2 is diagram illustrating a human gait simplified by a spring-mass model according to at least one example embodiment.

FIG. 2 is diagram illustrating a human gait simplified by a spring-mass model according to at least one example embodiment.

Referring to FIG. 2, when each leg of a person is understood as a single linear spring, a motion of the leg in a gait cycle may be simplified based on one degree of freedom. For example, a center of gravity of the person may be assumed to be located at a mass m and the leg may be assumed as a spring having a modulus of elasticity K. In a gait motion of the person, the motion of the leg may be acknowledged based on a change in straight-line distance from a portion of the leg, for example, a thigh to a ground and a change in elastic force following the change in straight-line distance. By using such structure, one-degree-of-freedom operational power corresponding to a distance between the thigh and the ground may be provided. In this example, the distance between the thigh and the ground and a force applied from a foot of the person to the ground, for example, a ground reaction force (GRF) may be adjusted so as to assist the gait of the person. Although FIG. 2 illustrates a spring has the modulus of elasticity K corresponding to a set value, the modulus of elasticity K may also be changed by adjusting the operational power.

Figure 3:
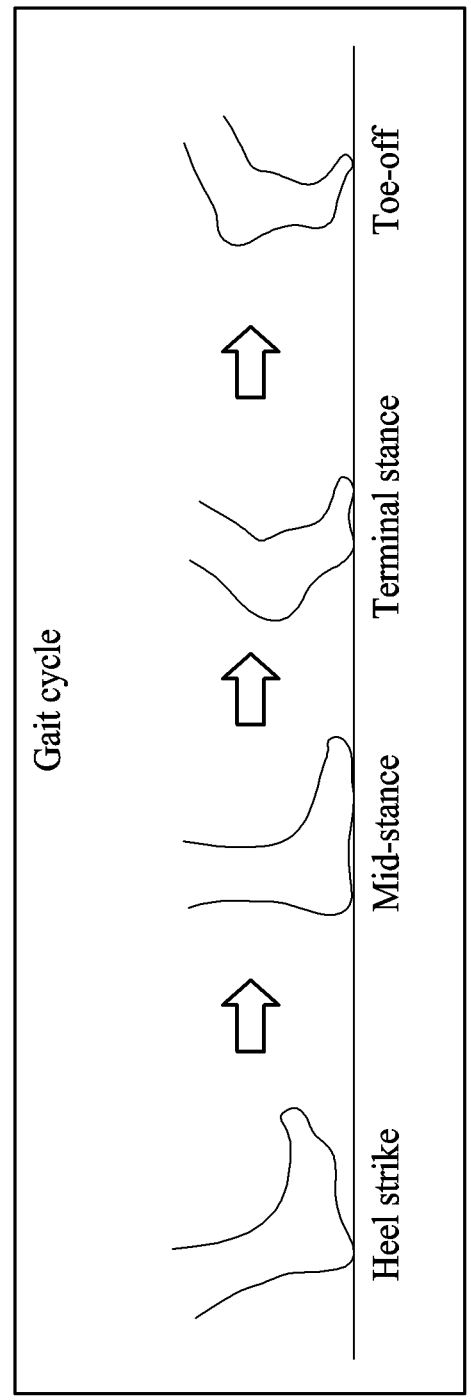
FIG. 3 is a diagram illustrating a portion of a human foot contacting a ground in a stance phase according to at least one example embodiment.

FIG. 3 is a diagram illustrating a portion of a human foot contacting a ground in a stance phase according to at least one example embodiment.

Referring to FIG. 3, it is understood that a portion of a foot of a person contacting a ground is sequentially changed in a stance phase during a gait. The stance phase may include a heel strike interval in which a heel contacts the ground, a mid-stance interval in which a sole contacts the ground, a terminal stance interval in which a forefoot contacts the ground, and a toe-off interval in which the forefoot pushes the ground off such that a person moves forward. In the stance phase, the foot may contact the ground sequentially from the heel to the forefoot. In such process, a center of pressure of the person with respect to the ground may move sequentially from the heel to the forefoot. Thus, to implement an actual gait of the person, a center of pressure of a motion assistance apparatus with respect to the ground may need to be moved sequentially from the heel to the forefoot.

Figure 4:
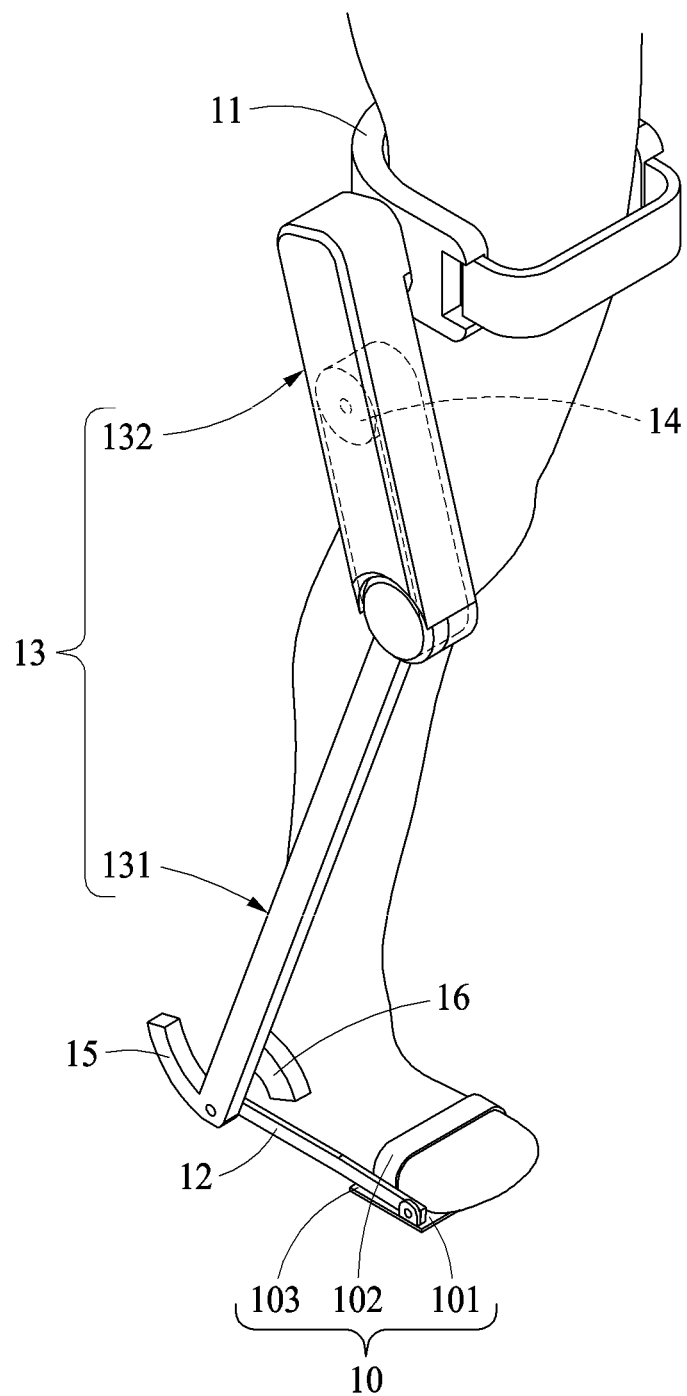
FIG. 4 is a perspective view of a motion assistance apparatus according to at least one example embodiment.
Figure 5:
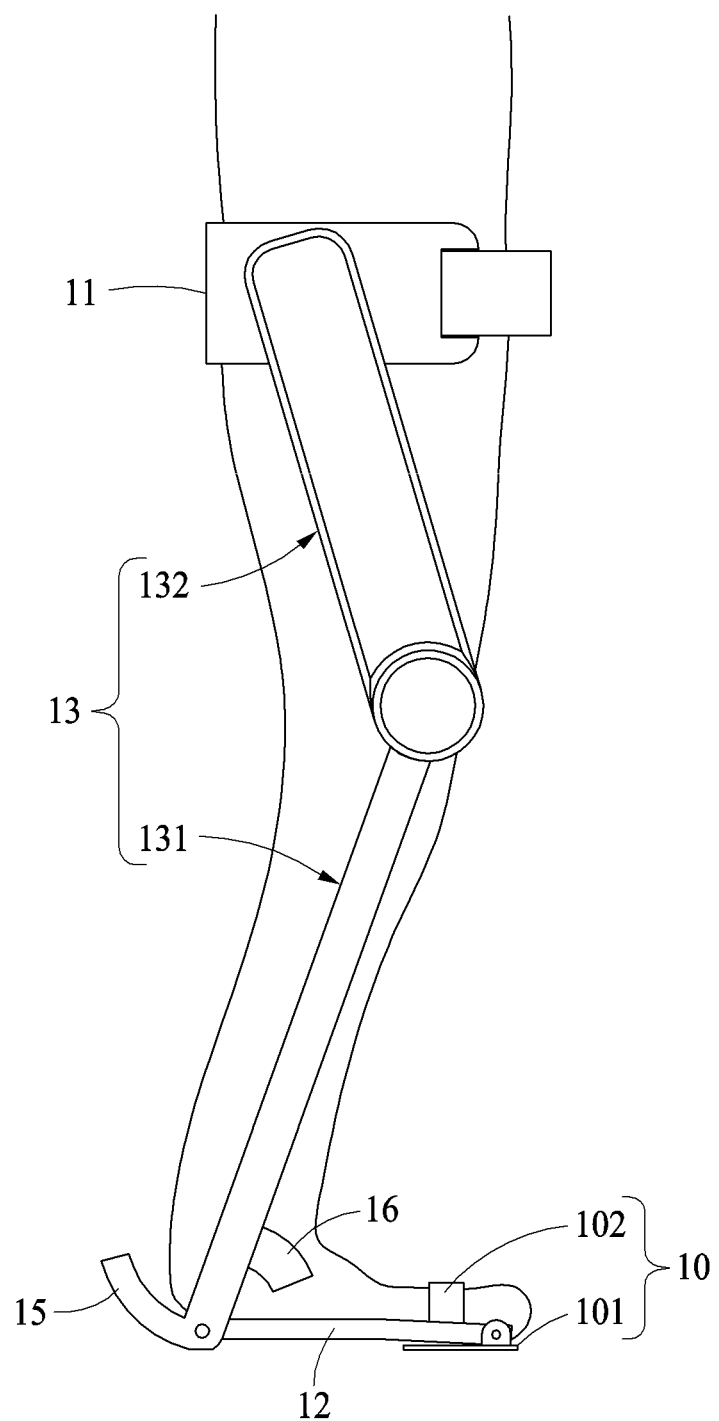
FIG. 5 is a side view of a motion assistance apparatus according to at least one example embodiment.
Figure 6:
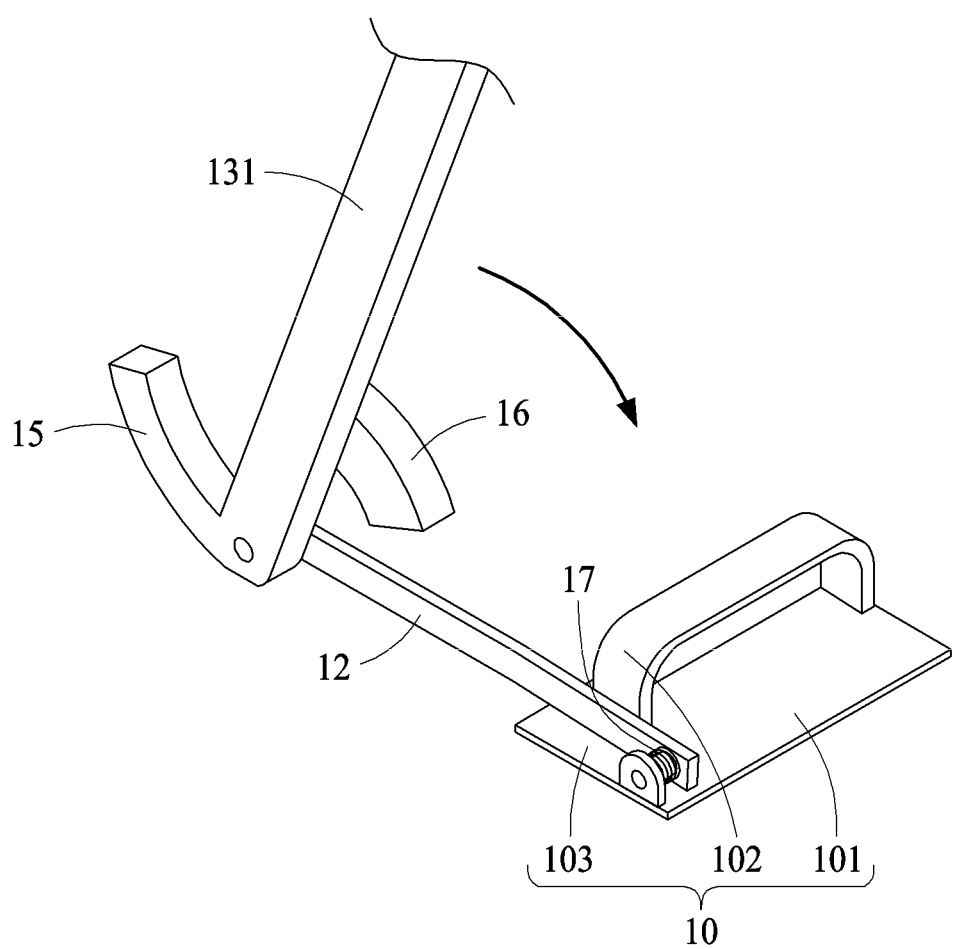
FIGS. 6 and 7 are perspective views of portions of a motion assistance apparatus according to at least one example embodiment.
Figure 7:
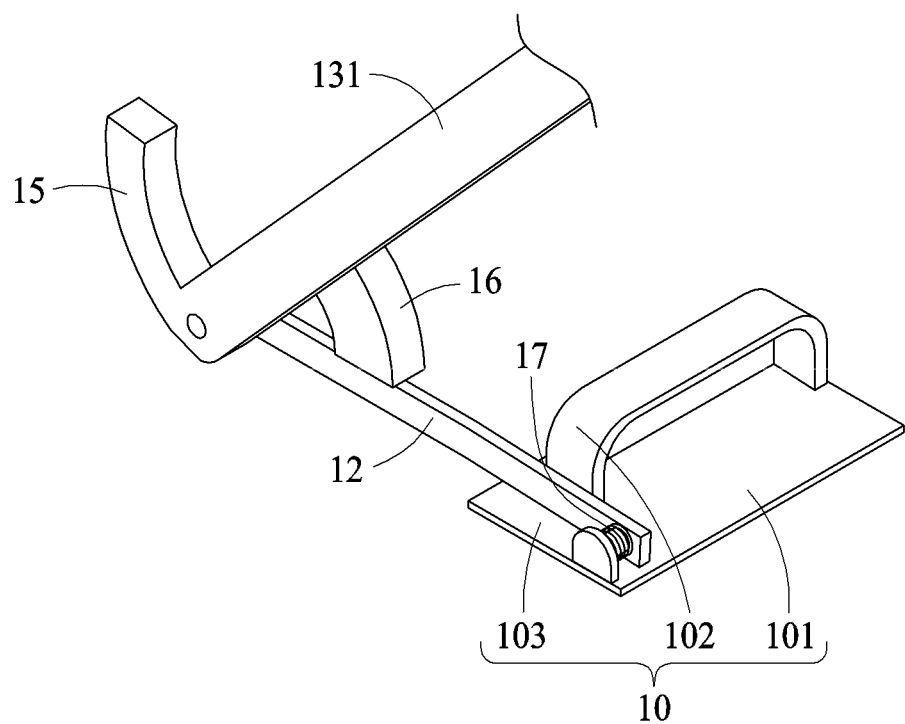

FIG. 4 is a perspective view of a motion assistance apparatus according to at least one example embodiment, FIG. 5 is a side view of a motion assistance apparatus according to at least one example embodiment, and FIGS. 6 and 7 are perspective views of portions of a motion assistance apparatus according to at least one example embodiment.

Referring to FIGS. 4 and 5, a motion assistance apparatus 1 may be worn by a user to assist a motion of the user. The user may correspond to a human, an animal, or a robot. However, the user is not limited thereto. Although FIGS. 4 and 5 illustrate a case in which the motion assistance apparatus 1 assists a gait motion of the user, the motion assistance apparatus 1 may also assist a motion of another portion of the user, for example, a wrist, an elbow, or a shoulder. That is, the motion assistance apparatus 1 may assist a motion of a portion of the user. Hereinafter, an example in which the motion assistance apparatus 1 assists a gait of a human will be described.

The motion assistance apparatus 1 may include a first support 10, a second support 11, a connection link 12, a distance adjustment assembly 13, an actuator 14, a heel guide 15, and a rotation preventer 16.

The first support 10 may support a first part of the user. The first part may be, a part contacting a ground, for example, a forefoot of the user when the user is walking. The first support 10 may include a sole support member 101, a wearable member 102, and a dropping preventer 103 arranged on a bottom of a foot of the user.

The sole support member 101 may support at least a portion, for example, a front portion of a sole of the user. In this example, the first support 10 may not contact the ground in a heel-strike interval of a stance phase. The wearable member 102 may be connected to the sole support member 101 and cover the forefoot of the user.

The dropping preventer 103 may support a portion of the connection link 12. For example, the dropping preventer 103 may extend from the first support 10 toward the connection link 12. In such structure, the dropping preventer 103 may prevent the connection link 12 from dropping due to a self-weight.

The second support 11 may support a second part of the user. The second part may be a portion above a knee joint, for example, a thigh. A plurality of joints including the knee joint and an ankle joint may be between the first part and the second part. Although the drawing illustrates that the second support 11 supports the thigh of the user, example embodiments are not limited thereto. The second support 11 may also support a portion above the thigh, for example, a waist or a chest. Hereinafter, an example in which the second support 11 supports the thigh of the user will be described for brevity of description.

The connection link 12 may be rotatably connected to the first support 10. The connection link 12 may be a longitudinal member extending from a forefoot to a heel of the user. A connection point between the connection link 12 and the first support 10 may be in front of a metatarsophalangeal joint. For example, the connection point between the connection link 12 and the first support 10 may be located on a side of the forefoot. In such structure, when the user performs a toe-off motion, the connection link 12 may rotate relative to the first support 10.

The distance adjustment assembly 13 may adjust a distance between the second support 11 and the connection link 12. First and second ends of the distance adjustment assembly 13 may be rotatably connected to the second support 11 and the connection link 12, respectively. Through this, the distance adjustment assembly 13 may adjust a relative distance between the first support 10 and the second support 11. The distance adjustment assembly 13 may include a first adjustment link 131 and a second adjustment link 132.

The first adjustment link 131 may reduce a shock received in the heel in at least a portion of intervals in an initial stage of the stance phase. Here, the initial stage of the stance phase may be intervals of the stance phase other than a push-off interval, that is, intervals from a heel-strike interval to a mid-stance interval.

The first adjustment link 131 may be rotatably connected to the connection link 12. When the user is wearing the motion assistance apparatus 1, a portion connecting the first adjustment link 131 and the connection link 12 may be between the forefoot and the heel. For example, the first adjustment link 131 may be configured to rotate relative to the connection link 12 between the forefoot and the heel. Such structure may reduce a difference between a center of pressure of the motion assistance apparatus 1 with respect to the ground and a center of pressure of a person in an actual gait in a mid-stance interval of the stance phase in comparison to a case in which the portion connecting the first adjustment link 131 and the connection link 12 is formed on one of the forefoot or the heel.

The second adjustment link 132 may connect the first adjustment link 131 and the second support 11. One end of the second adjustment link 132 may be connected to be movable relative to the first adjustment link 131. For example, the one end of the second adjustment link 132 may be rotatably connected to the first adjustment link 131. Likewise, the other end of the second adjustment link 132 may be rotatably connected to the second support 11. In this example, in response to a relative movement of the first adjustment link 131 and the second adjustment link 132, a relative distance between the connection link 12 connected to the first adjustment link 131 and the second support 11 connected to the second adjustment link 132 may be adjusted.

The actuator 14 may provide a power to rotate at least one of the first adjustment link 131 and the second adjustment link 132. Through this, the actuator 14 may adjust an angle between the first adjustment link 131 and the second adjustment link 132, and/or provide a torque to the first adjustment link 131 and the second adjustment link 132. The actuator 14 may be disposed between the first adjustment link 131 and the second adjustment link 132. As illustrated in FIG. 4, for example, the actuator 14 may be disposed in a portion connecting the first adjustment link 131 and the second adjustment link 132. In such structure, the power provided by the actuator 14 may be transmitted directly to a connection axis between the first adjustment link 131 and the second adjustment link 132. Thus, the power may be efficiently transmitted and a structural stability may be secured. Unlike the drawing, it is also possible to provide the actuator 14 on another position of the motion assistance apparatus 1 such that the power is transmitted via a power transmitting member to the first adjustment link 131 and the second adjustment link 132.

The heel guide 15 may assist a heel-strike motion of the user. The heel guide 15 may extend from the distance adjustment assembly 13 in a direction opposite to the connection link 12 so as to be located close to the heel of the user when the user is wearing the motion assistance apparatus 1. The heel guide 15 may be connected to one side of the first adjustment link 131. The heel guide 15 may have an arc shape curved upward as a distance from the distance adjustment assembly 13 increases. The heel guide 15 may also be shaped in, for example, a circle or an oval including an arc. In such structure, the heel guide 15 may be in rolling contact with the ground during the heel-strike interval through the mid-stance interval while the user is walking. In the heel-strike interval, the heel guide 15 may contact the ground to absorb a shock exerted on the heel of the user, and guide a contacting point between the motion assistance apparatus 1 and the ground naturally to be the portion connecting the first adjustment link 131 and the connection link 12. When the portion connecting the first adjustment link 131 and the connection link 12 is between the forefoot and the heel, the heel guide 15 located close to the heel in the heel-strike interval may be applied to be the center of pressure of the motion assistance apparatus 1 with respect to the ground. Thus, a difference between the center of pressure of the motion assistance apparatus 1 and the center of pressure of the user with respect to the ground may be reduced in an actual heel-strike motion of the user.

The rotation preventer 16 may limit a reduced (or, alternatively, a minimum) angle between the first adjustment link 131 and the connection link 12 to assist a toe-off motion of the user.

While FIGS. 4 and 5 illustrate an embodiment in which the distance adjustment assembly 13 is on a lateral side of the leg, example embodiments are not limited thereto. For example, in some example embodiments, the motion assistance apparatus 1 may include two distance adjustment assemblies 13 each having an actuator associated therewith, where a first distance adjustment assembly is on the lateral side of the leg of the user and a second distance adjustment assembly is on the medial side of the leg of the user. Therefore, since each leg is powered by two actuators, the motion assistance apparatus 1 may provide greater power and increased stability to the leg of the user.

FIGS. 6 and 7 are perspective views of portions of a motion assistance apparatus according to at least one example embodiment.

Referring to FIGS. 6 and 7, the rotation preventer 16 may allow the first adjustment link 131 and the connection link 12 to interfere with each other. Through this, the rotation preventer 16 may prevent the connection link 12 from rotating by an angle less than the minimum angle relative to the first adjustment link 131. For example, the rotation preventer 16 may be connected to at least one of the first adjustment link 131 and the connection link 12 so as to be located between the first adjustment link 131 and the connection link 12. Hereinafter, an example in which the rotation preventer 16 extends from the first adjustment link 131 will be described with reference to FIGS. 6 and 7.

As illustrated in FIG. 7, at a time at which a distance between the first support 10 and the second support 11 is reduced sufficiently, for example, in a toe-off interval of a gait of the user, the rotation preventer 16 extending from the first adjustment link 131 may be in contact with the connection link 12 such that the first adjustment link 131 and the connection link 12 perform a single rigid body motion. In this example, when the actuator 14 provides a power to the distance adjustment assembly 13 to increase the distance between the second support 11 and the first support 10, the first adjustment link 131 and the connection link 12 may rotate relative to the first support 10. The rotation preventer 16 may transfer the power applied to the distance adjustment assembly 13 to the connection link 12 such that the connection link 12 rotates relative to the first support 10. Through this, the rotation preventer 16 may assist the toe-off motion of the user.

The rotation preventer 16 may include a shock-absorbing member to absorb a shock occurring when the first adjustment link 131 and the connection link 12 perform a rigid body motion. The shock-absorbing member may be a member that is of, for example urethane and provided on one end of the rotation preventer 16 facing the connection link 12. In this example, the shock-absorbing member may absorb a shock occurring when an angle between the first adjustment link 131 and the connection link 12 is minimized and the first adjustment link 131 and the connection link 12 interfere with each other. Accordingly, the shock-absorbing member may reduce a shock exerted on a leg of the user in the toe-off interval.

The motion assistance apparatus 1 may include an elastic body 17 to interfere with the connection link 12 splaying from the first support 10. The elastic body 17 may be, for example, a torsion spring located in a portion connecting the first support 10 and the connection link 12. In such structure, the connection link 12 may be prevented from an undesired (or, alternatively, an unnecessary) movement, for example, wobbling against or splaying from the first support 10 in a state, for example, the swing phase. Through this, noise which may be generated during a user of the motion assistance apparatus 1 may be reduced and a stability of the motion assistance apparatus 1 may also be improved.

Referring to FIGS. 4 through 7, the motion assistance apparatus 1 may assist a gait of a user using one-degree-of-freedom power and implement motions similar to the heel-strike motion and the toe-off motion of the user, thereby providing an enhanced wearability to the user.

Figure 8:
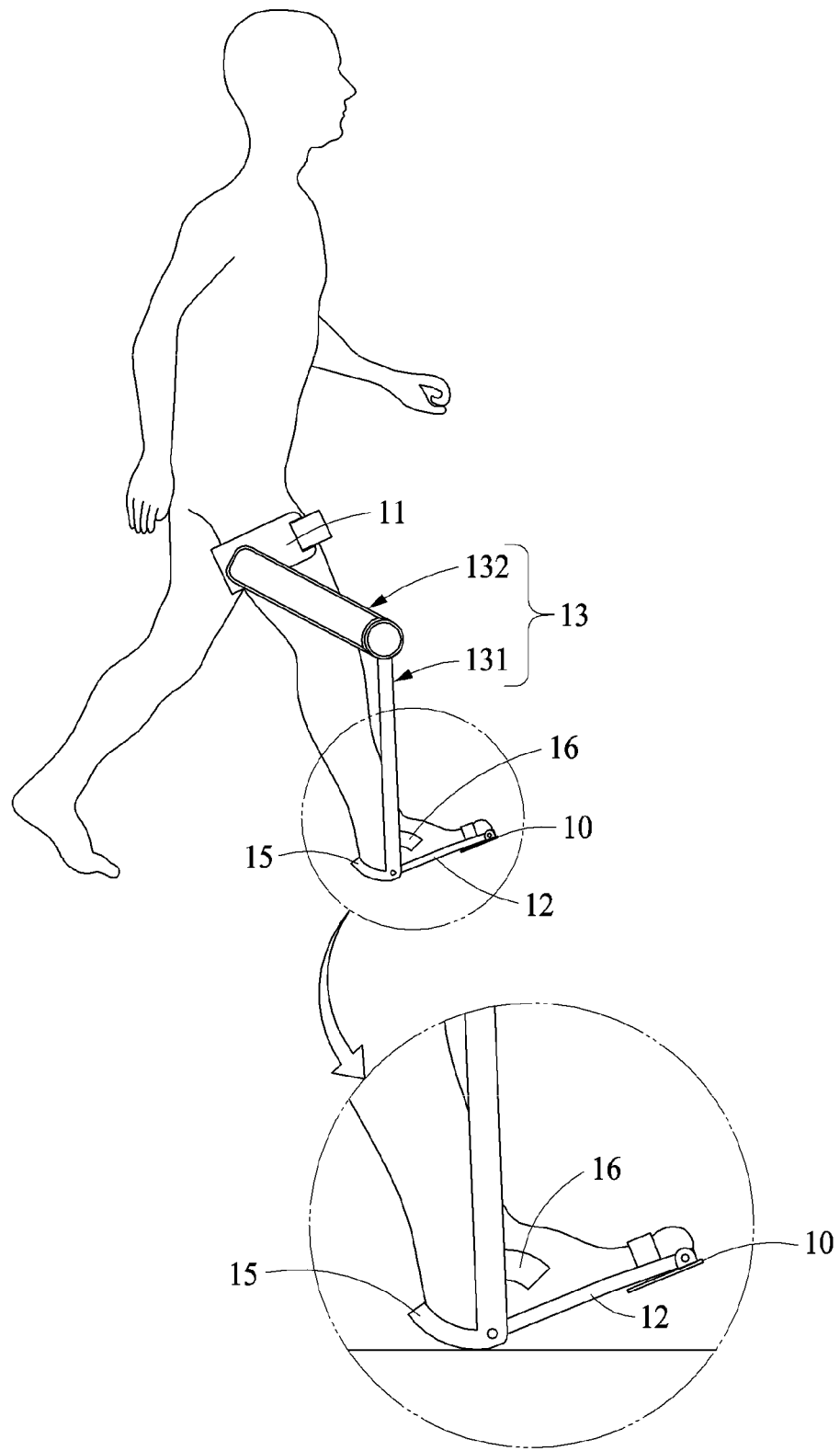
FIG. 8 illustrates an operation of a motion assistance apparatus in a heel strike interval according to at least one example embodiment.
Figure 9:
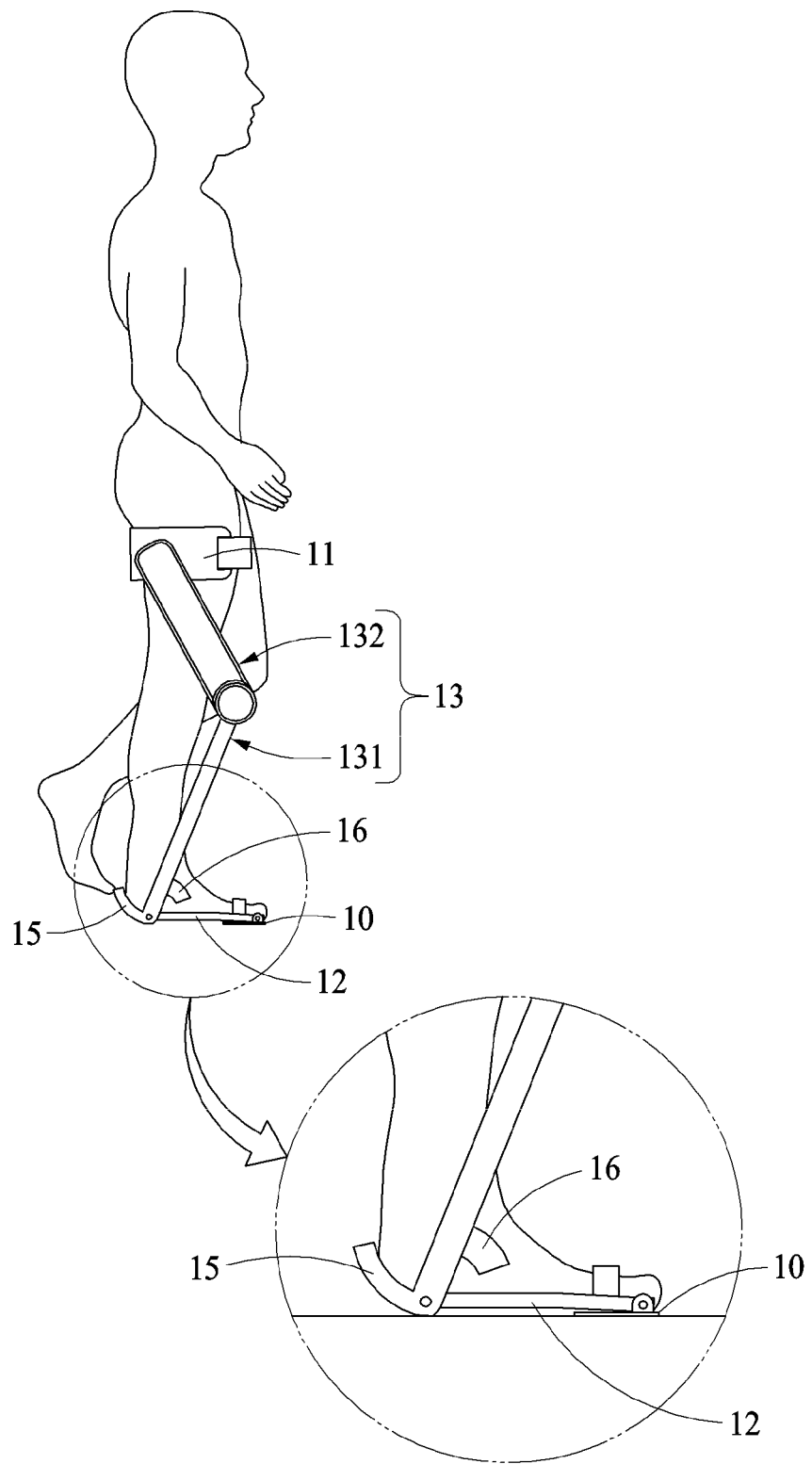
FIG. 9 illustrates an operation of a motion assistance apparatus in a mid-stance interval according to at least one example embodiment.
Figure 10:
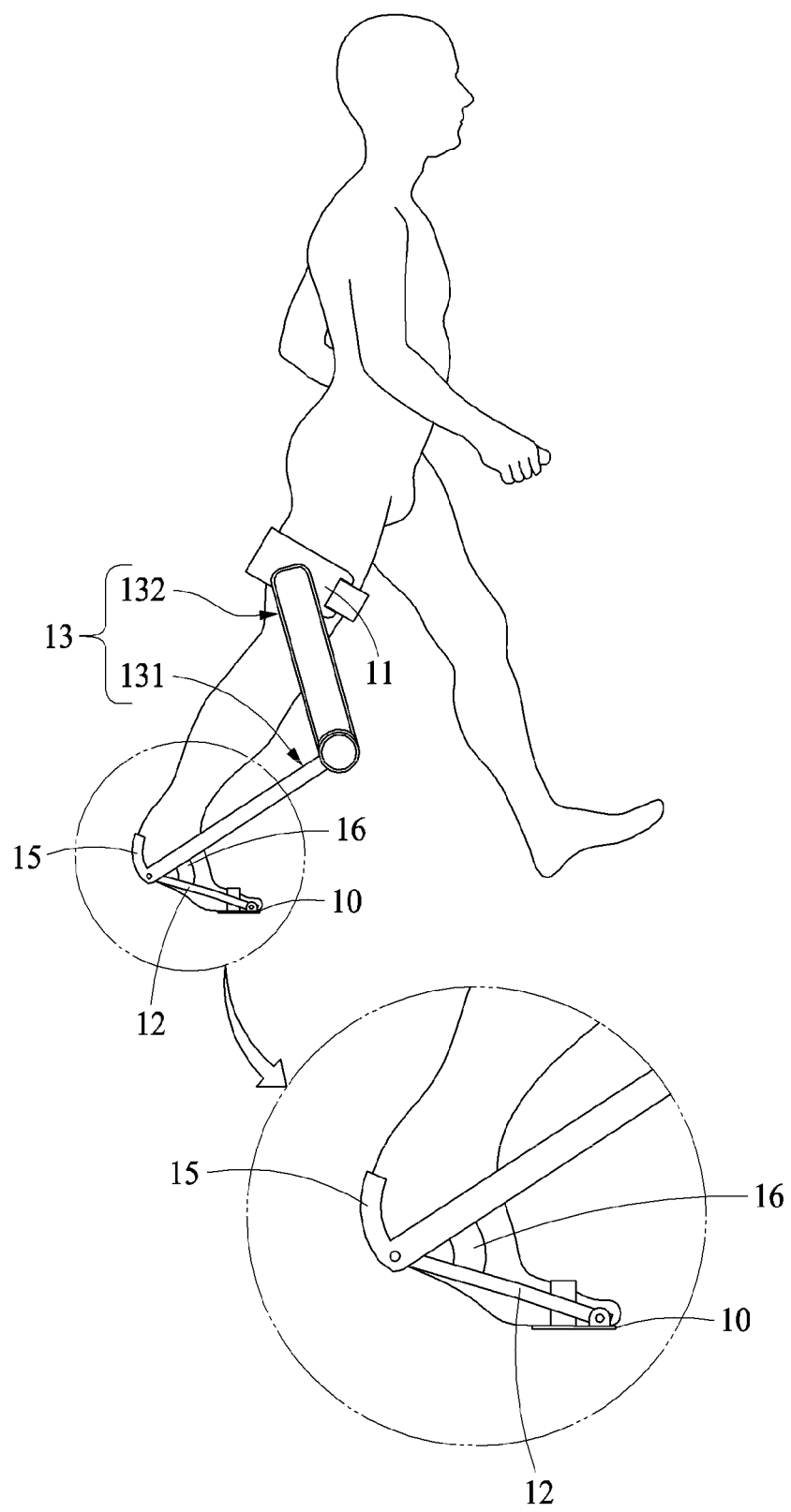
FIG. 10 illustrates an operation of a motion assistance apparatus in a terminal-stance interval according to at least one example embodiment.
Figure 11:
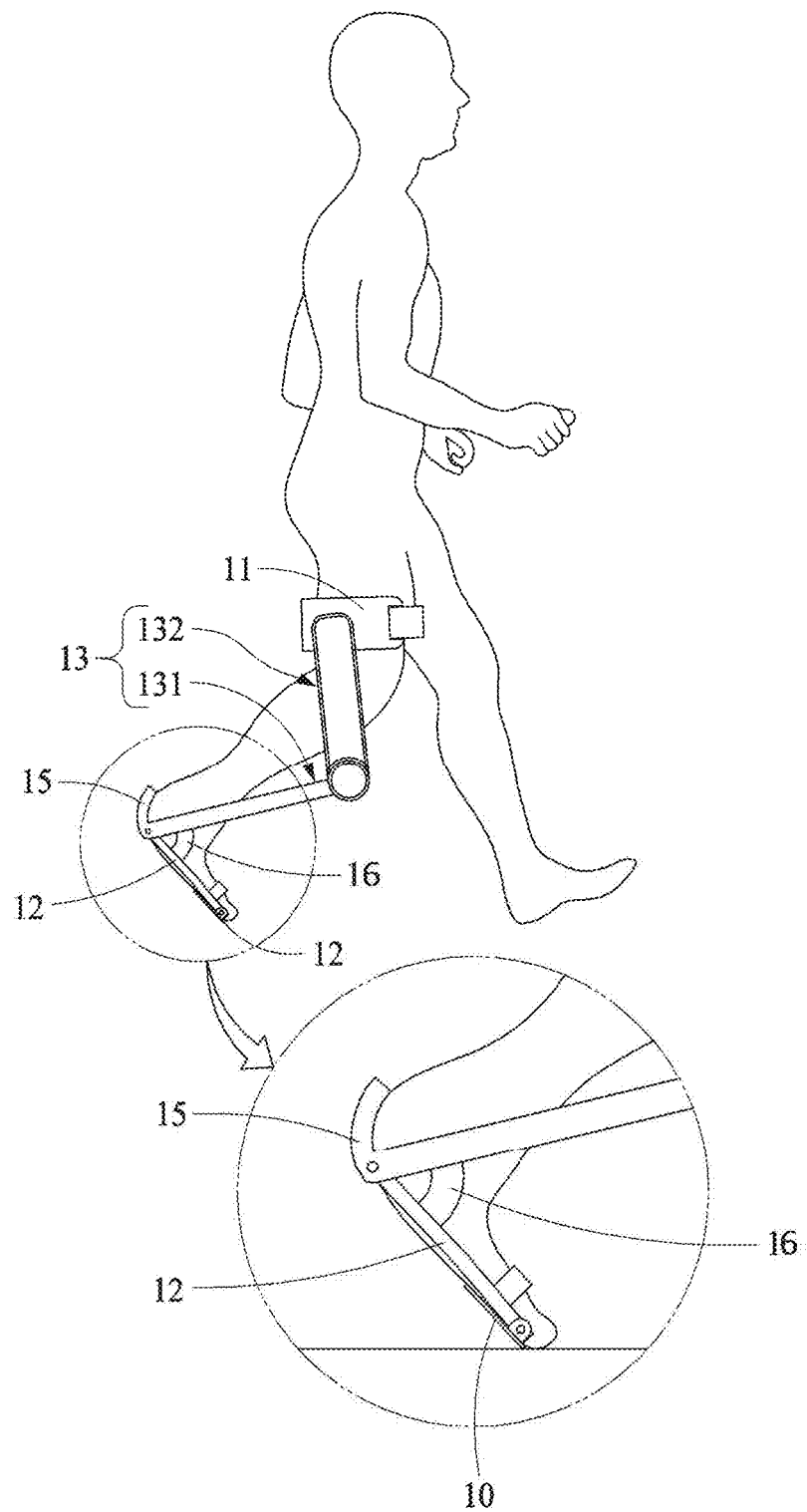
FIG. 11 illustrates an operation of a motion assistance apparatus in a toe-off interval according to at least one example embodiment.
Figure 12:
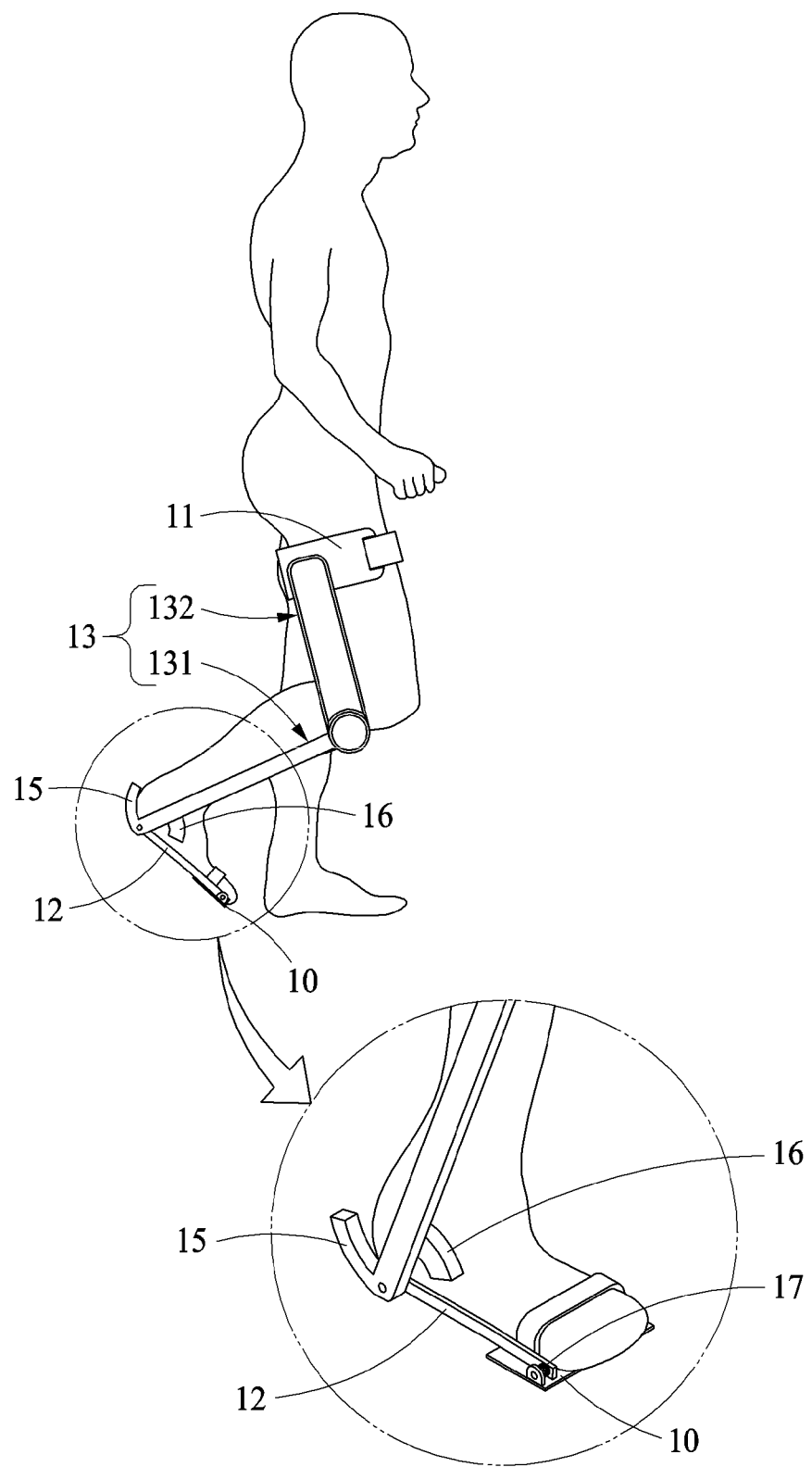
FIG. 12 illustrates an operation of a motion assistance apparatus in a swing interval according to at least one example embodiment.

FIG. 8 illustrates an operation of a motion assistance apparatus in a heel strike interval according to at least one example embodiment, FIG. 9 illustrates an operation of a motion assistance apparatus in a mid-stance interval according to at least one example embodiment, FIG. 10 illustrates an operation of a motion assistance apparatus in a terminal-stance interval according to at least one example embodiment, FIG. 11 illustrates an operation of a motion assistance apparatus in a toe-off interval according to at least one example embodiment, and FIG. 12 illustrates an operation of a motion assistance apparatus in a swing interval according to at least one example embodiment.

Referring to FIGS. 8 through 12, the motion assistance apparatus 1 may implement motions similar to an actual gait of a user while assisting a gait of the user using one-degree-of-freedom power.

As illustrated in FIG. 8, a leg of the user may contact a ground using the first adjustment link 131 or the heel guide 15 in a heel-strike interval. In this example, the actuator 14 may provide a power to the distance adjustment assembly 13 to increase a distance between the connection link 12 and the second support 11. The motion assistance apparatus 1 may reduce a shock occurring when a heel of the user touches the ground.

Referring to FIGS. 8 and 9, while the gait is continued from the heel-strike interval to a mid-stance interval, the heel guide 15 may be in rolling contact with the ground and guide an end portion of the first adjustment link 131 of the motion assistance apparatus 1 to smoothly contact the ground such that a center of pressure of the motion assistance apparatus 1 with respect to the ground is moved. In this example, the connection link 12 of the motion assistance apparatus 1 may rotate relative to the first adjustment link 131 and allow the first support 10 to contact with the ground.

As illustrated in FIG. 9, in the mid-stance interval, the leg of the user may contact the ground using the first adjustment link 131 or the first support 10. When the first adjustment link 131 and the first support 10 contact the ground simultaneously, the center of pressure of the motion assistance apparatus 1 may be between the first adjustment link 131 and the first support 10. In the mid-stance interval, the rotation preventer 16 may not allow the connection link 12 and the first adjustment link 131 to interfere with each other and thus, a dorsiflexion motion of an ankle may be freely performed.

As illustrated in FIG. 10, when a gait motion of the user enters a terminal stance interval from the mid-stance interval, an angle between the first adjustment link 131 and the connection link 12 may be reduced (or, alternatively, minimized). Also, rotation preventer 16 may allow the connection link 12 and the first adjustment link 131 to interfere with each other so as to perform a single rigid body motion. In this example, a center of gravity of the user may move to a portion of a forefoot, and a heel may be spaced apart from the ground. That is, while the user is walking, the motion assistance apparatus 1 may tilt forward the user and thus, the heel guide 15 may be spaced apart from the ground. Also, the connection link 12 mutually interfering with the first adjustment link 131 may rotate relative to the first support 10. Accordingly, the motion assistance apparatus 1 may contact the ground using only the first support 10 supporting the forefoot of the user.

As illustrated in FIG. 11, when the connection link 12 and the first adjustment link 131 perform the single rigid body motion, the actuator 14 may provide a power to the distance adjustment assembly 13 to increase a distance between the connection link 12 and the second support 11. For example, the actuator 14 may rotate the first adjustment link 131 and the second adjustment link 132 to increase an angle between the first adjustment link 131 and the second adjustment link 132. In such structure, the power provided by the actuator 14 may be applied to a portion connecting the first support 10 and the connection link 12 such that the first adjustment link 131 and the connection link 12 rotate relative to the first support 10 being in contact with the ground. Through this, the actuator 14 may assist the toe-off motion of the user.

As illustrated in FIG. 12, when the gait enters the swing phase from the stance phase, the motion assistance apparatus 1 may prepare for a stance phase in a new cycle. In the swing phase, the dropping preventer 103 and the elastic body 17 may allow the connection link 12 to be in close contact with the first support 10. The dropping preventer 103 may support a portion of the connection link 12 to be prevented from dropping. The elastic body 17 may interfere with the connection link 12 splaying from the first support 10.

Figure 13:
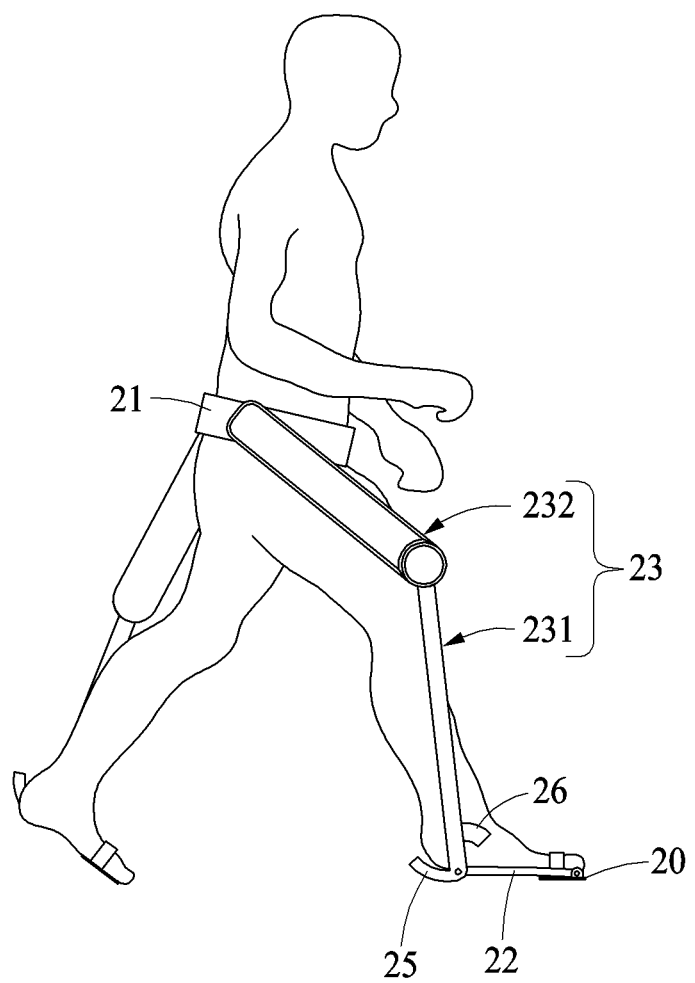
FIG. 13 is a side view of a motion assistance apparatus according to at least one example embodiment.
Figure 14:
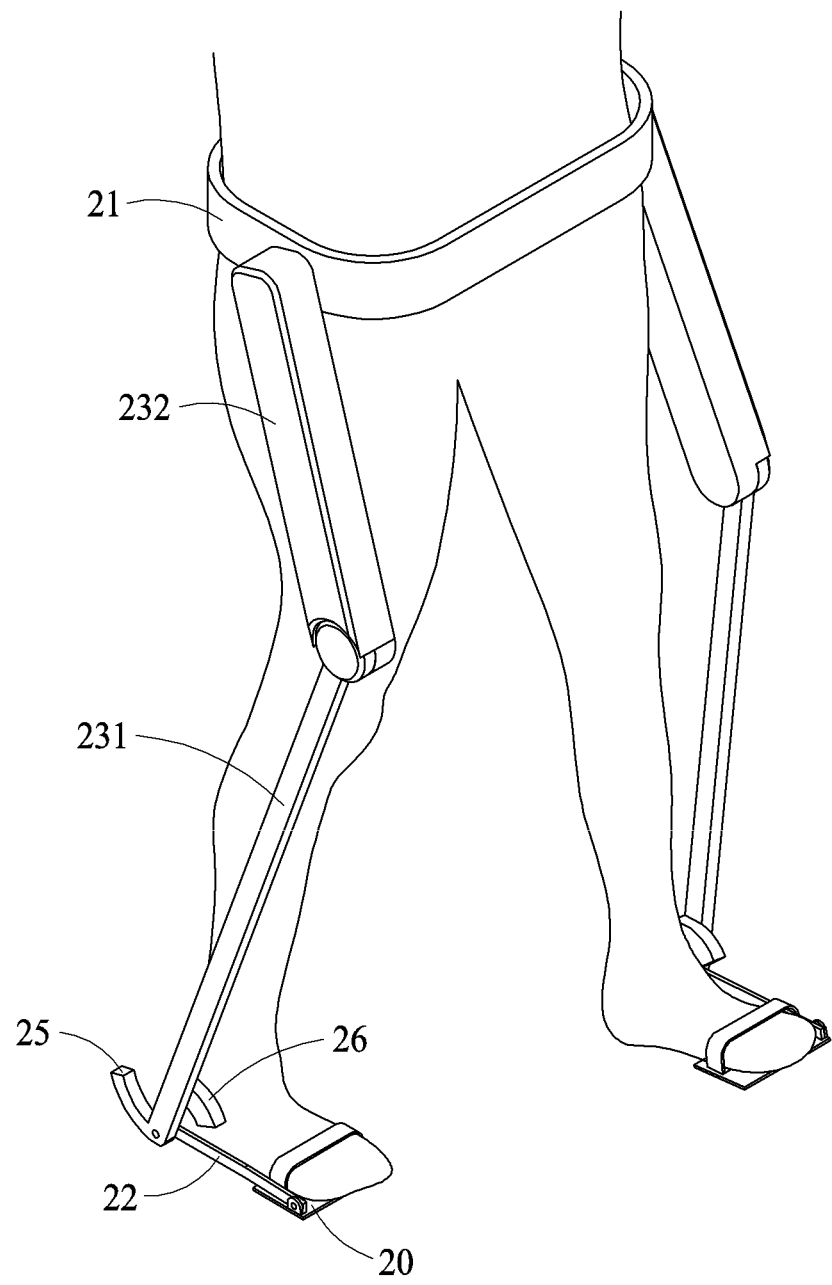
FIG. 14 is a perspective view of a motion assistance apparatus according to at least one example embodiment.

FIG. 13 is a side view of a motion assistance apparatus according to at least one example embodiment and FIG. 14 is a perspective view of a motion assistance apparatus according to at least one example embodiment.

Referring to FIGS. 13 and 14, a motion assistance apparatus 2 may include a first support 20, a second support 21, a connection link 22, a distance adjustment assembly 23, a heel guide 25, and a rotation preventer 26.

The second support 21 may support a portion above a knee joint, for example, a waist of a user. In this example, the motion assistance apparatus 2 may use the distance adjustment assembly 23 to adjust a distance between the connection link 22 disposed on a foot of the user and the second support 21 disposed on the waist of the user. The motion assistance apparatus 2 may assist a motion of a leg between the connection link 22 and the second support 21 using one-degree-of-freedom power.

Figure 15:
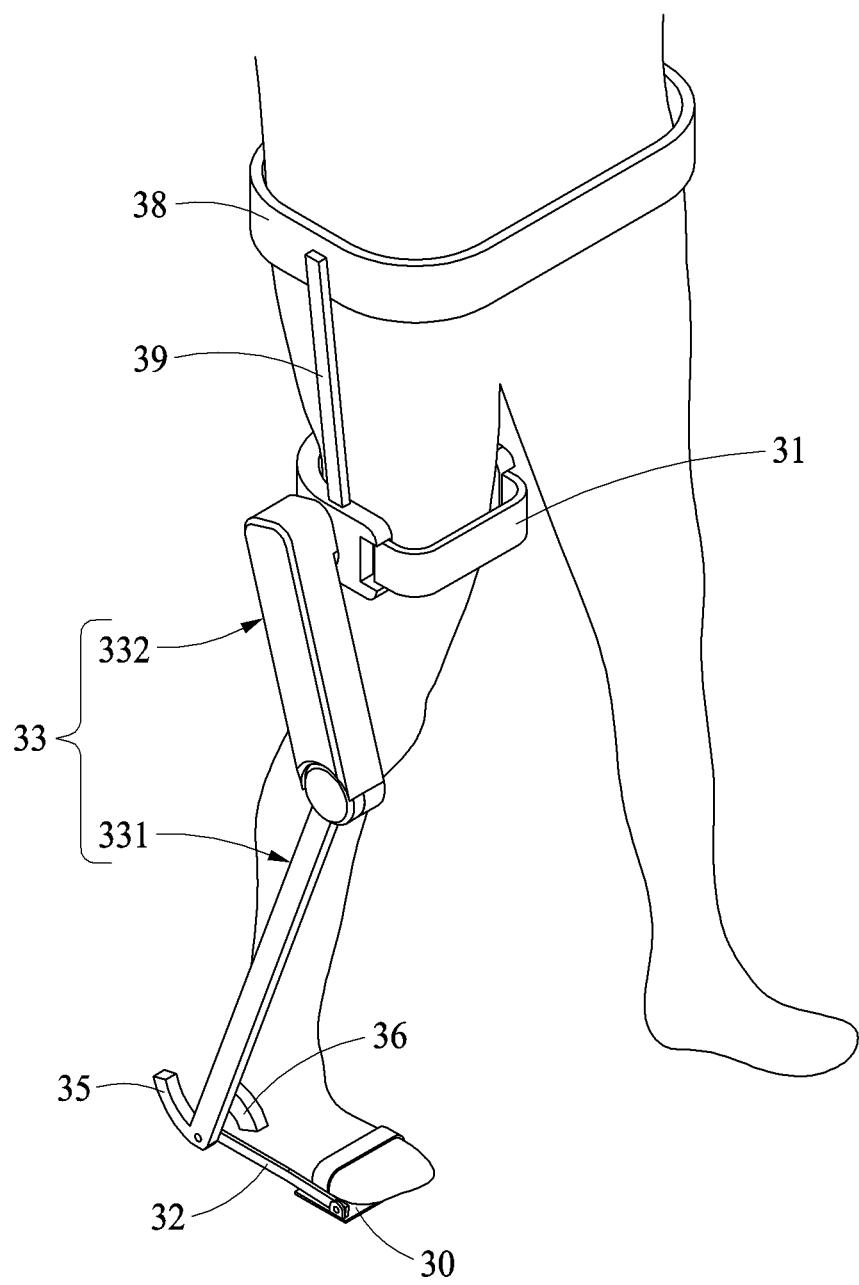
FIG. 15 is a perspective view of a motion assistance apparatus according to at least one example embodiment.

FIG. 15 is a perspective view of a motion assistance apparatus according to at least one example embodiment.

A motion assistance apparatus 3 may include a first support 30, a second support 31, a connection link 32, a distance adjustment assembly 33, a heel guide 35, a rotation preventer 36, a third support 38, and a connecting member 39.

The third support 38 may support a third part of a user. The third part may be located on an opposite side of a first part supported by the first support 30 based on a second part supported by the second support 31. For example, when the first support 30 and the second support 31 respectively support a forefoot and a thigh of the user, the third support 38 may support a waist of the user.

The connecting member 39 may connect the third support 38 and the second support 31. The connecting member 39 may be a longitudinal member that extends from the third support 38 to the second support 31. The connecting member 39 may be, for example, a frame as illustrated in FIG. 14, or a member such as a wire, a rubber string, and the like.

The third support 38 and the connecting member 39 may prevent a separation of the second support 31 from the second part of the user while the user is waling. Through this, the motion assistance apparatus 3 may stably assist a motion of the user.

Figure 16:
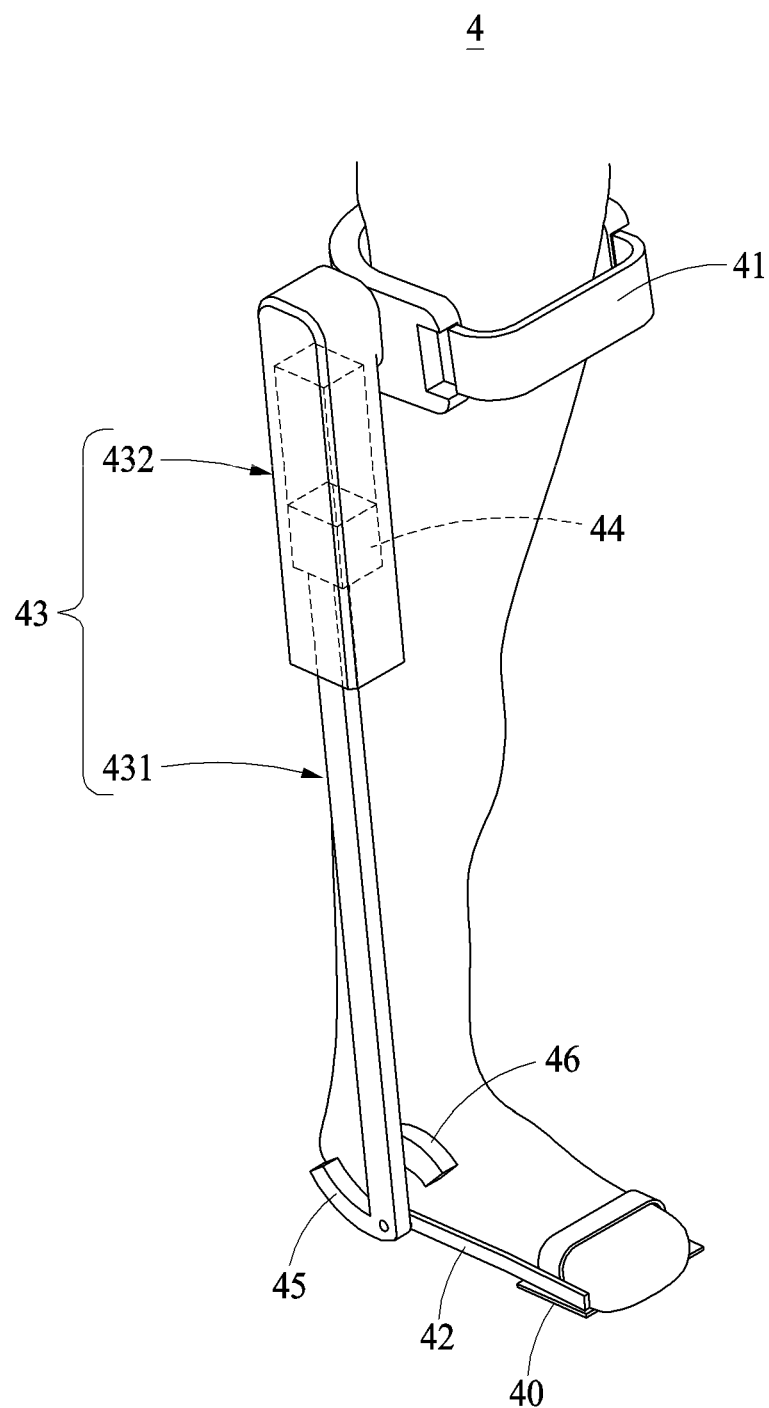
FIG. 16 is a perspective view of a motion assistance apparatus according to at least one example embodiment.
Figure 17:
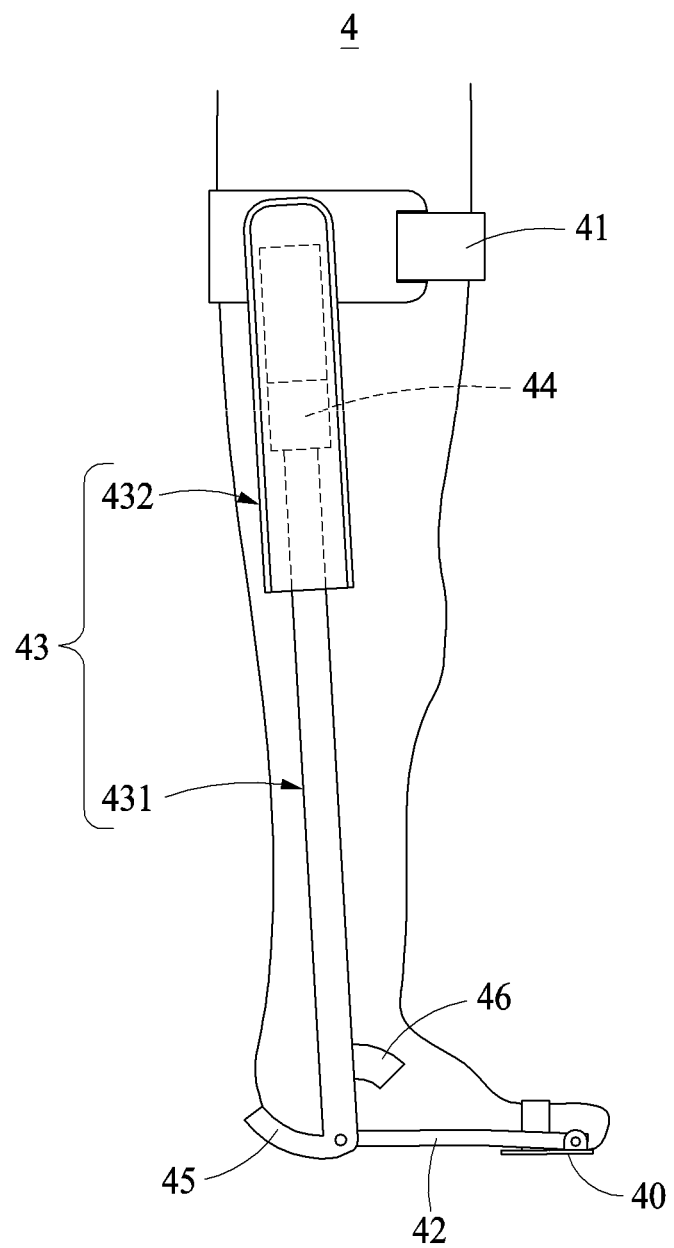
FIG. 17 is a side view of a motion assistance apparatus according to at least one example embodiment.

FIG. 16 is a perspective view of a motion assistance apparatus according to at least one example embodiment and FIG. 17 is a side view of a motion assistance apparatus according to at least one example embodiment.

Referring to FIGS. 16 and 17, a motion assistance apparatus 4 may include a first support 40, a second support 41, a connection link 42, a distance adjustment assembly 43, an actuator 44, a heel guide 45, and a rotation preventer 46.

The distance adjustment assembly 43 may include a first adjustment link 431 rotatably connected to the connection link 42 and a second adjustment link 432 rotatably connected to the second support 41. The first adjustment link 431 and the second adjustment link 432 may be connected such that a distance between the first adjustment link 431 and the second adjustment link 432 is adjustable relative to each other. For example, a relative distance may be linearly adjusted when the second adjustment link 432 slides with respect to the first adjustment link 431.

The actuator 44 may include a linear actuator to connect the first adjustment link 431 and the second adjustment link 432 and provide a power such that the first adjustment link 431 and the second adjustment link 432 slide relative to each other. For example, the actuator 44 may be disposed inside the second adjustment link 432 and move along a guide rail included in the second adjustment link 432 so as to allow the first adjustment link 431 to perform a linear motion.

The motion assistance apparatus 4 may adjust a distance between the second support 41 and the connection link 42 through a sliding movement of the distance adjustment assembly 43. In this example, since the distance adjustment assembly 43 has a linear operation range, the motion assistance apparatus 4 may effectively assist a gait of the user wearing the motion assistance apparatus 4 even when an operation area around the user is limited.

Figure 18:
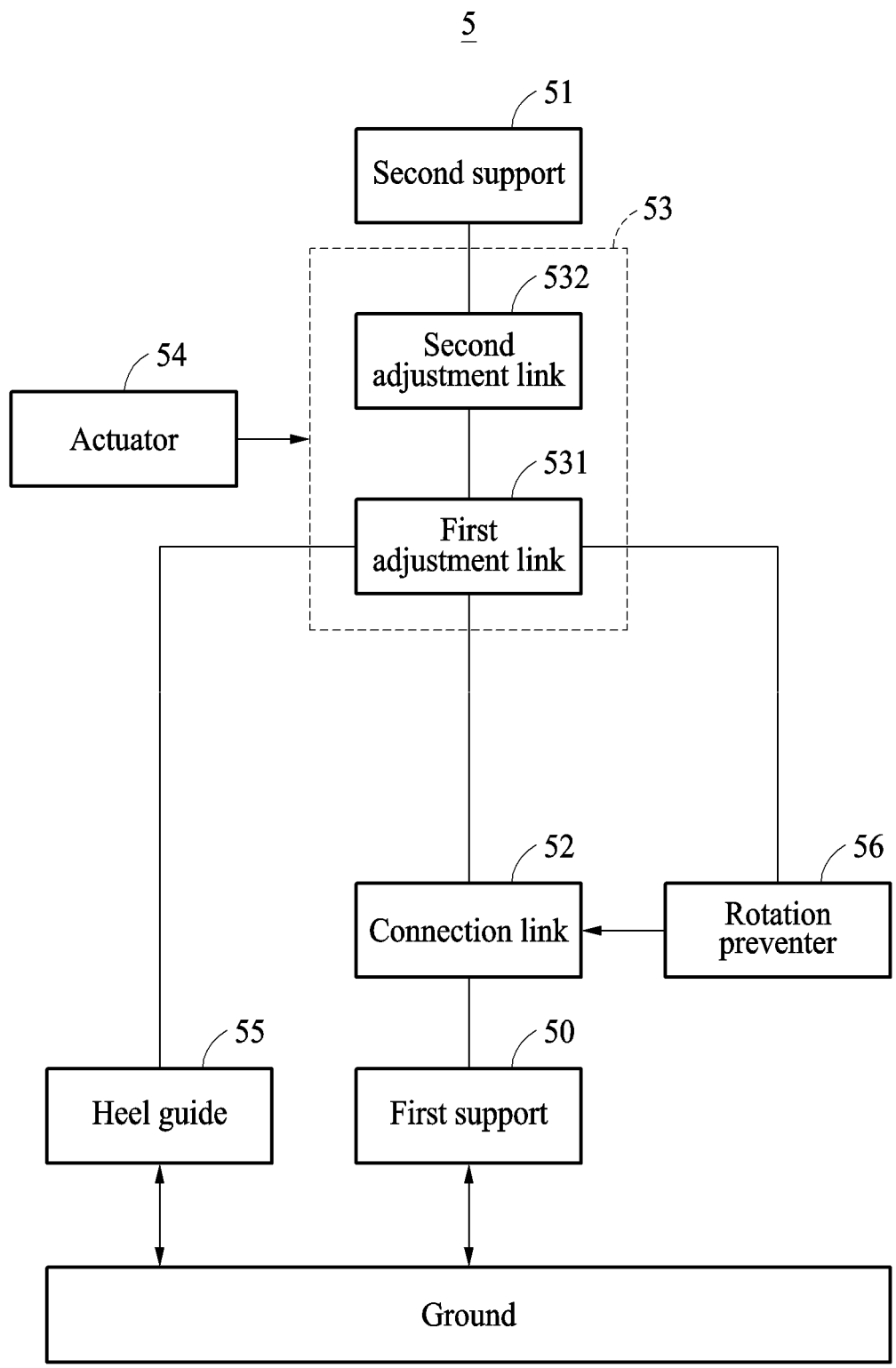
FIG. 18 is a block diagram illustrating a motion assistance apparatus according to at least one example embodiment.
Figure 19:
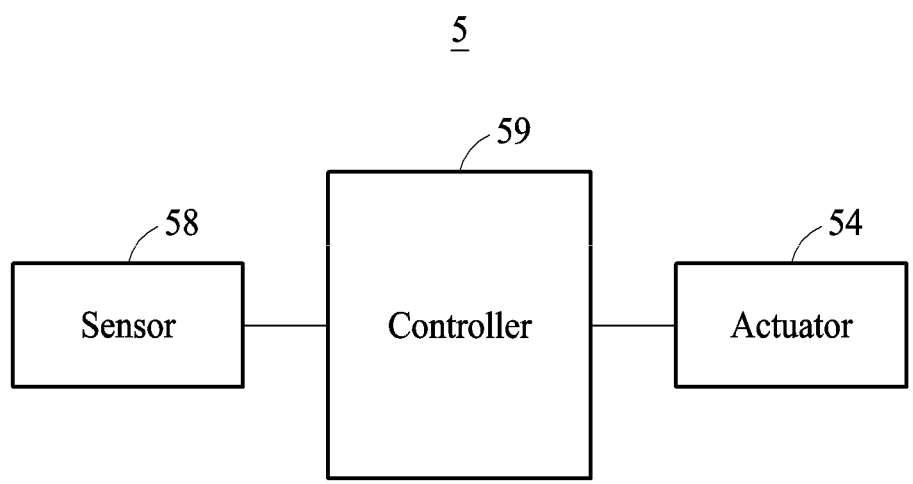
FIG. 19 is a block diagram illustrating a motion assistance apparatus according to at least one example embodiment.
Figure 20:
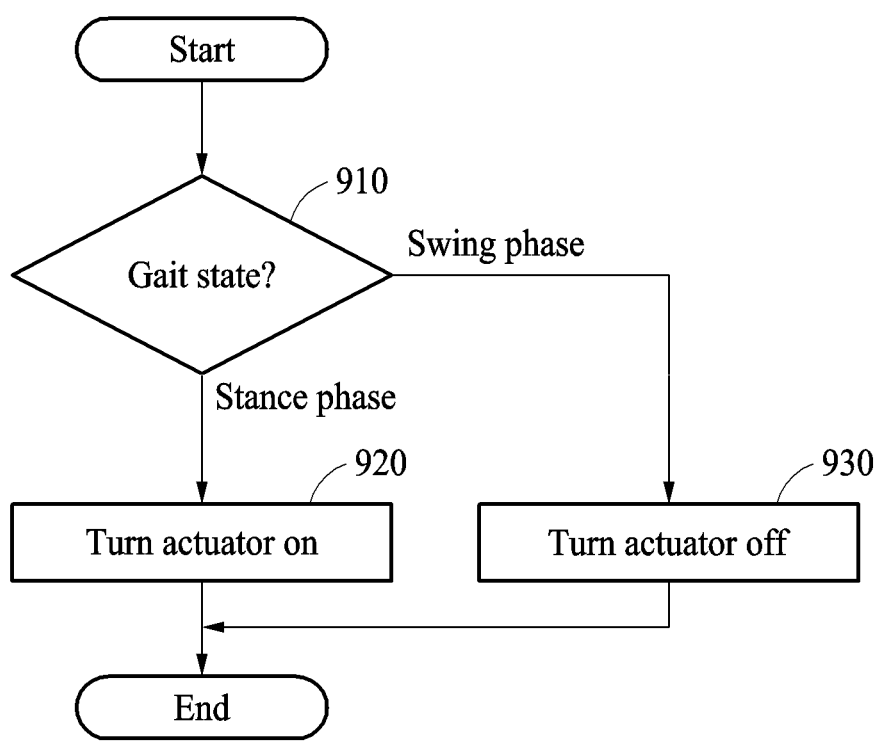
FIG. 20 is a flowchart illustrating a control method of a motion assistance apparatus according to at least one example embodiment.

FIG. 18 is a block diagram illustrating a motion assistance apparatus according to at least one example embodiment, FIG. 19 is a block diagram illustrating a motion assistance apparatus according to at least one example embodiment, and FIG. 20 is a flowchart illustrating a control method of a motion assistance apparatus according to at least one example embodiment.

Referring to FIGS. 18 and 19, a motion assistance apparatus 5 may assist a user with walking using an operation power based on one degree of freedom. The motion assistance apparatus 5 may include a first support 50, a second support 51, a connection link 52, a distance adjustment assembly 53, an actuator 54, a heel guide 55, a rotation preventer 56, a sensor 58, and a controller 59. The distance adjustment assembly 53 may include a first adjustment link 531 and a second adjustment link 532.

The actuator 54 may provide a power to allow the first adjustment link 531 to move relative to the second adjustment link 532 so as to adjust a relative distance between the second support 51 and the connection link 52, or provide a torque or a force exerted on the first adjustment link 531 and the second adjustment link 532. Through this, the motion assistance apparatus 5 may assist a gait motion of the user using one-degree-of-freedom power based on, for example, a linear spring model as described with reference to FIG. 3.

The motion assistance apparatus 5 may contact a ground using the heel guide 55 or the first support 50. Based on a feature of a human foot, a point of the foot contacting the ground may be sequentially changed in the stance phase. The motion assistance apparatus 5 may use the heel guide 55 to contact the ground in the heel strike interval, and use the first support 50 to contact the ground in the terminal stance interval and the toe-off interval. In this example, a change in center of pressure of the motion assistance apparatus 5 may be similar to a change in center of pressure of the user with respect to the ground in an actual gait. Accordingly, the motion assistance apparatus 5 may implement a motion similar to the actual gait of the user while assisting the gait of the user using one-degree-of-freedom power, thereby providing a natural gait assistance.

The motion assistance apparatus 5 may selectively actuate the actuator 54 based on a gait cycle of a user.

The actuator 54 may provide a power to the distance adjustment assembly 53 and adjust a distance between the second support 51 and the connection link 52 during the gait of the user. For example, the actuator 54 may provide the power to the distance adjustment assembly 53 to increase a distance between the second support 51 and the connection link 52 in a stance phase.

The sensor 58 may sense a gait cycle of the user. The sensor 58 may detect whether the heel guide 55 or the first support 50 contacts a ground to sense the gait cycle of the user. For example, the sensor 58 may include a pressure sensor, an inertial measurement unit, or an acceleration sensor disposed on the foot to sense whether the foot contacts the ground. When a pressure sensed by the pressure sensor increases, the pressure sensor may detect that the foot contacts the ground. Also, a vibration occurring when the foot touches the ground may be sensed by the inertial measurement unit or the acceleration sensor.

When the heel guide 55 or the first support 50 contacts the ground, the sensor 58 may sense the gait cycle as the stance phase. When the heel guide 55 and the first support 50 are spaced apart from the ground, the sensor 58 may sense the gait cycle as the swing phase.

The controller 59 may control the actuator 54 based on information sensed by the sensor 58.

The controller may include a memory and processing circuitry.

The memory may include may include a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion.

The processing circuitry may include a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

The processing circuitry may be configured, through a layout design and/or execution of computer readable instructions stored in the memory, as a special purpose computer to control the actuator 54 based on signals received from the one or more sensors 58.

For example, in some example embodiments, the controller 59 may determine whether the user is in a stance phase or a swing phase based on the signals from the one or more sensors 58.

In some example embodiments, the controller 59 may enable the actuator 54 to rotate to assist a heel-strike motion and/or a toe-off motion of the user, if the controller 59 determines that the leg is in a stance phase, and may disable the actuator 54 to allow the user freely move a leg, if the controller 59 determines that the leg is in the swing phase.

Referring to FIG. 20, a control method of the motion assistance apparatus 5 may include operation 910 to sense a gait state, operation 920 to turn an actuator on, and operation 930 to turn the actuator off.

In operation 910, the controller 59 may sense a gait state of a user using the sensor 58.

When the controller 59 senses that the gait state is a stance phase in operation 910, the controller 59 may turn the actuator 54 on so as to assist a heel-strike motion or a toe-off motion of the user.

When the controller 59 senses that the gait state is a swing phase in operation 910, the controller 59 may turn the actuator 54 off such that the user freely moves a leg.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assistance apparatus comprising:
   a first support configured to support a first part of a user;
   a connection link rotatably connected to the first support;
   a second support configured to support a second part of the user;
   a distance adjustment assembly including a first adjustment link and a second adjustment link, the first adjustment link rotatably connected to the connection link at a first connection point and the second adjustment link rotatably connected to the second support at a second connection point, the first adjustment link and the second adjustment link being rotatably connected via a joint therebetween, the motion assistance apparatus being unsecured to the user between the first connection point and the second connection point such that a linear distance between the first connection point and the second connection point varies via rotation of the joint; and
      a rotation limiter rigidly connected to one of the first adjustment link or the connection link.

2. The motion assistance apparatus of claim 1, wherein a first end and a second end of the distance adjustment assembly are rotatably connected to the connection link and the second support, respectively.

3. The motion assistance apparatus of claim 1, further comprising:
   an actuator configured to generate a power to rotate the joint.

4. The motion assistance apparatus of claim 3, wherein the actuator is between the first adjustment link and the second adjustment link.

5. The motion assistance apparatus of claim 1, wherein the second adjustment link is slidably connected to the first adjustment link.

6. The motion assistance apparatus of claim 5, further comprising:
   a linear-actuator configured to connect the first adjustment link and the second adjustment link.

7. The motion assistance apparatus of claim 1, wherein the rotation limiter is configured to limit an angle between the first adjustment link and the connection link by selectively contacting a second one of the first adjustment link and the connection link in response to the angle reaching a minimum amount.

8. The motion assistance apparatus of claim 7, further comprising:
   an actuator configured to drive the distance adjustment assembly, wherein
      the first adjustment link and the connection link are configured to perform a single rigid body motion and the connection link is configured to rotate relative to the first support, when an angle between the first adjustment link and the connection link is the minimum angle while the actuator is driven.

9. The motion assistance apparatus of claim 8, wherein the rotation limiter includes a shock-absorbing member configured to absorb a shock occurring when the first adjustment link and the connection link perform the single rigid body motion.

10. The motion assistance apparatus of claim 1, wherein the first support includes a dropping preventer configured to support a portion of the connection link.

11. The motion assistance apparatus of claim 1, further comprising:
    an elastic body configured to provide an elastic force to interfere with the connection link splaying from the first support.

12. The motion assistance apparatus of claim 1, further comprising:
    a third support configured to support a third part of the user located on an opposite side of the user from the second part; and
    a connecting member configured to connect the third support and the second support.

13. The motion assistance apparatus of claim 1, wherein the first support is configured to support a forefoot of the user and the second support is configured to support a thigh or a portion above the thigh of the user.

14. The motion assistance apparatus of claim 13, wherein a portion connecting the distance adjustment assembly and the connection link is located between the forefoot and a heel of the user when the user is wearing the motion assistance apparatus.

15. The motion assistance apparatus of claim 14, further comprising:
    a heel guide configured to extend from the distance adjustment assembly in a direction opposite to the connection link, and to contact a ground when the user performs a heel-strike motion.

16. The motion assistance apparatus of claim 15, wherein the heel guide has an arc shape curved upward as a distance from the distance adjustment assembly increases.

17. The motion assistance apparatus of claim 15, wherein
    in a heel strike interval, the heel guide is configured to contact the ground and the first support is configured to separate from the ground, and
    in a push-off interval, the heel guide is configured to separate from the ground and the first support is configured to contact the ground.

18. The motion assistance apparatus of claim 13, further comprising:
    a sensor configured to sense a gait cycle of the user; and
    a controller configured to control an actuator based on the gait cycle sensed by the sensor such that the controller is configured to turn the actuator on in a stance phase, and to turn the actuator off in a swing phase.

* * * * *